United States Patent [19]

Onwumere et al.

[11] Patent Number: 5,328,698

[45] Date of Patent: Jul. 12, 1994

[54] METHOD FOR RENDERING A SUBSTRATE SURFACE ANTITHROMBOGENIC AND/OR ANTI-INFECTIVE

[75] Inventors: Fidelis C. Onwumere, Miamisburg; Donald D. Solomon, Spring Valley; Stanley C. Wells, Dayton, all of Ohio

[73] Assignee: Becton, Dickinson and Company, Franklin Lakes, N.J.

[21] Appl. No.: 563,653

[22] Filed: Aug. 6, 1990

[51] Int. Cl.$^5$ ............................................. A61K 47/30
[52] U.S. Cl. ................................. 424/486; 424/426; 424/473
[58] Field of Search ............... 424/423, 420, 473, 424, 424/486, 425, 426, 78, 83; 523/112; 604/266, 264, 265; 427/2

[56] References Cited

U.S. PATENT DOCUMENTS

| | | | |
|---|---|---|---|
| 3,617,344 | 11/1971 | Leininger | 424/422 X |
| 3,634,123 | 1/1972 | Eriksson | 424/422 X |
| 3,695,921 | 10/1972 | Shepard et al. | 424/422 |
| 3,810,781 | 5/1974 | Eriksson et al. | 525/54.2 |
| 4,349,467 | 9/1982 | Williams et al. | 525/54.2 |
| 4,456,543 | 6/1984 | Owens | 252/106 |
| 4,479,795 | 10/1984 | Mustacich et al. | 604/53 |
| 4,521,564 | 6/1985 | Solomon et al. | 525/54.1 |
| 4,581,028 | 4/1986 | Fox, Jr. et al. | 525/54.1 |
| 4,587,266 | 5/1986 | Verdicchio | 514/635 |
| 4,678,660 | 7/1987 | McGary et al. | 424/25 |
| 4,713,402 | 12/1987 | Solomon | 523/112 |
| 4,822,615 | 4/1989 | Iwata et al. | 424/423 |
| 4,865,870 | 9/1989 | Hu et al. | 427/2 |
| 4,925,668 | 5/1990 | Khan et al. | 424/422 |
| 4,939,007 | 7/1990 | Hu et al. | 428/34.1 |
| 4,983,170 | 1/1991 | Etheredge, III et al. | 604/270 |
| 4,999,210 | 3/1991 | Solomon et al. | 424/78 X |

FOREIGN PATENT DOCUMENTS

WO 86/02561 5/1986 PCT Int'l Appl. .

OTHER PUBLICATIONS

*Petrothene Polyolefins—A Processing Guide*, Fifth Edition, 1986, p. 73 Michaeli, *Extrusion Dies*, p. 210, Hanser Publishers, New York, New York, 1984.

Primary Examiner—Thurman K. Page
Attorney, Agent, or Firm—Richard E. Brown

[57] ABSTRACT

A shaped medical article of a polymeric substrate is extrusion coated with a composition which includes a bioactive agent dispersed in a matrix polymer. Preferred bioactive agents are temperature sensitive agents which undergo thermal decomposition at a temperature above the processing temperature of the matrix polymer. Preferred matrix polymers have a melting point of about 100° C. or lower.

12 Claims, No Drawings

METHOD FOR RENDERING A SUBSTRATE SURFACE ANTITHROMBOGENIC AND/OR ANTI-INFECTIVE

BACKGROUND OF THE INVENTION

1. Field of the Invention

This invention relates to biomedical devices, and more specifically relates to a method for coating a substrate with an antithrombogenic and/or an anti-infective agent.

2. Background of the Invention

Extensive investigations have been undertaken over many years to find materials that will be biologically and chemically stable toward body fluids. This area of research has become increasingly important with the development of various objects and articles which must be in contact with blood, such as artificial organs, vascular grafts, probes, cannulas, catheters and the like.

Synthetic plastics have come to the fore as preferred materials for such articles. However, these materials have the major drawback of being thrombogenic. In addition, devices such as catheters provide a pathway for entrance of microorganisms into the body and thus often are a source of infection. Accordingly, much effort has been directed toward methods to render plastic medical devices antithrombogenic and anti-infective.

Thrombogenicity has conventionally been counteracted by the use of anticoagulants such as heparin. Various procedures for attachment of heparin to otherwise thrombogenic polymeric surfaces have been disclosed. U.S. Pat. No. 4,521,564 to Solomon et al. discloses coating a polymeric article with an amine-rich surface and covalently conjugating aldehyde-actuated heparin to the amino groups thereof. Leininger et al., in U.S. Pat. No. 3,617,344 discloses a method in which a polymeric surface is chemically modified to include a chloromethyl group. Amination of the chloromethyl group provides a quarternary ammonium halide. Reaction of the halide with sodium heparin results in ionic bonding of the heparin to the surface.

A related approach has been described by Eriksson et al. in U.S. Pat. No. 3,634,123. An article having a plastic surface is heated to near or above its softening point in an aqueous solution of a cationic surface active agent, such as a long chain alkylamine or alkylenediamine hydrohalide. The solution is preacidified to a pH of 7.0 or lower. Subsequent digestion of the plastic article with an aqueous solution of heparin results in an article having about 0.12 International Unit of heparin thereon. Improvements in the surface active agent method are described in U.S. Pat. No. 3,810,781 to Eriksson et al.; U.S. Pat. No. 4,349,467 to Williams et al.; U.S. Pat. No. 4,865,870 to Hu et al. and U.S. Pat. No. 4,713,402 to Solomon et al.

Attempts to solve the problem of infection have likewise been directed toward adherence of an antibacterial agent to the plastic article. Shepard et al., in U.S. Pat. No. 3,695,921, discloses dipping a catheter into a syrup containing a hydrophilic polymer and absorbing an antibiotic into the hydrophilic coating. Shepard et al. teach that most antibiotics are not sufficiently heat stable to be added to the syrup during the dipping step.

Fox et al. in U.S. Pat. No. 4,581,028, teaches infection resistant plastic medical articles, such as vascular grafts, having incorporated antimicrobial agents, such as silver sulfadiazine and pipericillin. The articles are prepared by dipping procedures.

Mustacich et al., in U.S. Pat. No. 4,479,795, discloses medical devices of permeable polymers including a releasably incorporated coating of a carboxylate antimicrobial agent. The device is made by a dipping process.

PCT published application no. WO 86/02561 teaches a medical device of a hydrophobic thermoplastic polymer having up to 1% chlorhexidine base coated thereon or incorporated therein.

McGary et al, in U.S. Pat. No. 4,678,660 discloses a method for preparing a polyurethane article having coated thereon a layer of polyurethane alloy containing a dispersed complex of a quaternary salt with either an antithrombogenic agent or an antibiotic. The method includes dipping the article in a solvent solution of the alloy.

Although all of the above disclosures have addressed the problems of infection and thrombogenesis during use of medical articles, satisfactory solutions have not yet been disclosed, particularly for medical articles, such as a catheter, to be introduced and advanced through body passages. In particular, there is a need for a method for preparation of medical articles coated with temperature sensitive materials which avoids dipping procedures using potentially toxic solvents. The present invention fulfills this need.

SUMMARY OF THE INVENTION

A method for applying a bioactive agent to the surface of a polymeric substrate includes preparing a composition having a bioactive agent uniformly dispersed in a melt of a matrix polymer and extrusion coating the composition onto the polymeric substrate. The uniform dispersion of the bioactive agent may be a solution or a suspension. In a preferred method, the composition is prepared by melt compounding the matrix polymer and bioactive agent.

The extrusion coating may be carried out within a processing temperature range defined herein as the temperature range between the melting point of the matrix polymer and the thermal decomposition point of the bioactive agent. The melting point of the matrix polymer is defined as the temperature at which the polymer becomes sufficiently fluid for extrusion.

Preferred matrix polymers have a melting point of about 120, most preferably about 100° C. or less and preferred bioactive agents are temperature sensitive, anti-infective and antithrombogenic agents which undergo thermal decomposition at a temperature above the melting point of the matrix polymer.

Prior to the present invention, the only method known for coating medical devices with temperature sensitive bioactive agents was by solvent coating. Solvent coating has many drawbacks which are eliminated by the extrusion coating of the invention. Solvent coating is a multi-step process which adds time and expense to a production line. Since most bioactive agents are not water soluble, expensive, high boiling organic solvents, such as dimethylacetamide must be used. The high boiling points of these solvents cause difficulty in removal. High vacuum is usually required, and this often leads to pitting of an article surface because of bubble formation. Such surfaces are rough and may lead to patient discomfort. Further, these solvents are generally toxic and complete removal is thus mandatory for medical articles intended for contact with a patient's tissue or body fluid.

In general terms, the method of the invention is an economical and efficient means of modifying surfaces to improve oxidation resistance, moisture resistance, gas impermeability, bacterial or fungal resistance, UV resistance and other forms of "host" plastic breakdown. For example, food or tissue contact plastics do not have good barrier properties against fungi and bacteria. However, extrusion coating with a polymer containing a suitable bioactive agent in accordance with the invention produces excellent fungal/bacterial barrier properties.

The extrusion coating method of the invention is of particular value in the coating of medical articles. With the method of the invention, the article may be extrusion fabricated of any high melting base polymer to provide desired mechanical properties, then extrusion coated with a bioactive agent at low temperature to modify the surface. Conventional extrusion of base polymer compounded with the bioactive agent cannot be carried out if the bioactive agent is temperature sensitive. Conversely, conventional coextrusion of base polymer with a low melting matrix polymer cannot be performed when there is a wide difference in processing temperatures between the base polymer and the matrix polymer. The method of the invention makes it possible to thermally coat the shaped base polymer without changing its configuration.

DETAILED DESCRIPTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments illustrated and described. The scope of the invention will be measured by the appended claims and their equivalents.

Coating of substrates with polymers is a conventional process in many industries. One common coating process applies a monomer to a substrate surface and polymerizes it in situ by exposure to a glow discharge, an electron beam, ultraviolet radiation or other procedure. In extrusion coating, on the other hand, a layer of polymer is applied directly to the substrate surface. In this process, a molten, homogeneous thermoplastic material is metered through a die directly onto a solid continuous shaped substrate surface such as paper, paperboard, film, foil, fabric or wire. General and specific descriptions of equipment and processing conditions for extrusion coating may be found in *Petrothene ® Polyolefins—A Processing Guide*, Fifth Edition, 1986, page 73 et seq. published by USI Chemicals, Division of National Distillers and Chemical Corp. A discussion of dies and equipment suitable for extrusion coating of wires wherein a melt flows around a hollow mandril through which a wire is passed is given by Michaeli in Extrusion Dies, Page 210 et seq., Hanser Publishers, New York, N.Y. (1984).

In accordance with the present invention, a shaped polymeric article is extrusion coated with a bioactive agent compounded in a thermoplastic matrix polymer. While the invention contemplates extrusion coating of any polymeric article, preferred substrates are shaped polymeric medical articles, most preferably articles intended for contact with a patient's tissue or body fluid. Representative non-limiting substrates are a tubing such as a catheter, a solid rod such as an obturator, and a sheet or porous membrane such as a graft or wound dressing.

The shaped medical article to be extrusion coated may be any thermoplastic or thermoset polymeric substrate. It may be fully cross-linked, slightly cross-linked or have no cross-linking. Preferred polymeric substrates have a melting point above the processing temperature of the matrix polymer.

The polymeric substrate serves as a support material for the matrix polymer and provides the article with whatever mechanical properties are desired, such as tensile strength, thermoplasticity and flexibility. The invention contemplates use of any polymeric or copolymeric substrate material which provides these attributes. The particular choice of substrate polymer and the shape thereof does not constitute a critical aspect of the invention. Suitable substrate polymers are polyacrylate, polystyrene, polyethylene, polypropylene, polytetrafluoroethylene, polyester, polyamide, and polyvinyl such as polyvinyl chloride and polyvinyl acetate. Preferred substrate polymers are thermoplastic polyurethanes, most preferably polyurethaneureas.

The choice of matrix polymer depends on the thermal stability of the desired bioactive agent. If the bioactive agent is thermally stable so that no substantial thermal degradation occurs during the extrusion coating, any thermoplastic matrix polymer may be used and the extrusion coating may be carried out at any suitable processing temperature.

A preferred application of the method of the invention is extrusion coating of temperature sensitive bioactive agents. For such agents, the matrix polymer preferably has a processing temperature below the decomposition temperature of the bioactive agent. The most preferred matrix polymers have a processing temperature of about 100° C. or less. The following list is merely representative and not limitative of matrix polymers which are suitable for extrusion coating of temperature sensitive agents. The melting points are given in parentheses.

| ethylene acrylic acid (15%, 20%) copolymer | (90° C.) |
|---|---|
| polycaprolactone | (60° C.) |
| polyethylene adipate | (55° C.) |
| polybutylene adipate | (54° C.) |
| polyethylene azeleate | (55° C.) |
| polyethylene methacrylic acid ionomer | (83° C.) |

It is evident that any anti-infective agent as known in the art, such as antibacterials, anti-microbials and germicides may be extrusion coated onto the shaped medical article if it is stable at the processing temperature of the matrix polymer. Thus the invention contemplates extrusion coating of thermally stable anti-infectives such as chlorhexidine and silver sulfadiazine. However, the method of the invention is particularly directed to anti-infectives which are temperature sensitive, most particularly those which undergo thermal decomposition during extrusion. Representative temperature sensitive anti-infectives which have heretofore been applied to a substrate surface only by solvent-based coating techniques but which may be extrusion coated in accordance with the present invention are methyl, propyl and butyl paraben, benzalkonium chloride, octenidine, alexidine, phenolic agents, triphenyl bismuthine, nitrophenyl acetate, silver, cetyl pyridinium chloride, bis pyridinamines and alkyl bis biguanides.

In the same way, the invention contemplates extrusion coating of any antithrombogenic agent as known in the art. The term antithrombogenic agent or material as used herein refers to any material which inhibits thrombus formation on its surface, such as by reducing platelet adhesion and/or aggregation, dissolving fibrin, enhancing passivating protein deposition, or inhibiting one or more steps within the coagulation cascade. Illustrative antithrombogenic materials may be selected from the group consisting of heparin, prostaglandins, sulfated polysaccharide, urokinase, dicumerol, warfarin, streptokinase, albumin and mixtures thereof. It should be understood that these materials are used in their natural form or as salts thereof, such as the sodium, or lithium salt or as chemically modified moieties. The preferred antithrombogenic agent is heparin which is temperature sensitive and heretofore has been coated onto medical devices only from solution.

In another embodiment of the matrix polymer containing the method of the invention, extrusion coating of a quaternary ammonium salt may be carried out. Any salt, such as those disclosed in U.S. Pat. No. 4,865,870 to Hu et al. for solvent coating onto a polymeric substrate may be used. Preferred salts are thermally stable at the processing temperature of the matrix polymer. Such salts are well-known to have some inherent antimicrobial activity. Preferably, they may be extrusion coated onto the shaped article to serve as a binder for antithrombogenic agents and anti-infective agents having a functional group which forms a complex with the salt.

Preferred antithrombogenic agents for this embodiment of the invention are sulfonated polysaccharides, such as dextran sulfate, or preferably a salt of heparin, such as sodium heparin. Preferred anti-infective agents for this embodiment of the invention are antibiotics bearing a functional group reactive with the quaternary salt, such as a carboxyl functionality. Exemplary materials may be selected from the group consisting of penicillin, oxacillin, ticarcillin, carbenicillin, cephalosporins, cefoxitin, cefazolin, dicloxacillin, cloxacillin and clavulanic acid, and mixtures thereof.

Reaction of the quaternary salt extrusion coated onto the substrate and the antithrombogenic or anti-infective agent may be carried out by steeping the article in an aqueous solution of the agent, as described in the aforementioned U.S. Pat. No. 4,865,870.

In preparation for extrusion coating, the bioactive agent of the invention may be compounded with the matrix polymer. Any compounding procedure as known in the art which does not cause degradation of the agent may be used. For example, if the agent is soluble, it may merely be dissolved in the matrix polymer melt. If it is not soluble, it may be dispersed in the melt as a suspension of finely divided particles.

In a preferred compounding technique, an intimate mixture of the bioactive agent and matrix polymer pellets is prepared by conventional procedures such as dusting or tumbling. The mixture may then be introduced into a compounding extruder from which it emerges as a homogenous melt directly into the coating extruder where it contacts the substrate.

Any desired ratio of bioactive agent and matrix polymer may be used. Preferably, the bioactive agent is combined with the matrix polymer in a weight percent ratio of about 1:5 to 1:100. Most preferably, a ratio of about 1:10 to 1:20 is used.

As is well known by those skilled in the art, the extrusion coating conditions may be adjusted to give a coating of any desired thickness. Preferred coatings are about 0.1 to 5.0 mils thick, most preferably about 1 to 2 mils.

EXAMPLE

General Procedure for Extrusion Coating

Pellets of the matrix polymer and finely powdered bioactive agent are tumbled together for about 10 minutes to give an even coating of the powder on the pellets. The coated pellets are charged into the hopper of a C. W. Brabender extruder with a mixing head and melt compounded. The melt is forced into a Killon extruder where it contacts and coats a polymeric article.

The following chart includes polyurethane tubes extrusion coated by the method of the invention and is provided merely by way of non-limiting examples.

| Matrix Polymer | Bioactive Agent (wt. %) | Extrusion Temp (°C.) | Coating Thickness (Mil) |
|---|---|---|---|
| 1. polycaprolactone | heparin (5) | 75 | 2.0 |
| 2. polycaprolactone | warfarin (5) | 115 | 1.5 |
| 3. polycaprolactone | dicumerol (6) | 120 | 1.5 |
| 4. polycaprolactone | chlorhexidine diacetate (6) | 120 | 1.5 |
| 5. ethylene acrylic acid (300 melt index) | chlorhexidine (6) | 115 | 2.0 |
| 6. polycaprolactone | benzalkonium chloride (6) | 120 | 2.1 |
| 7. ethylene acrylic acid (300 melt index) | benzalkonium chloride (6) | 120 | 2.1 |
| 8. polycaprolactone | methylparaben (6) | 120 | 1.5 |

What is claimed is:

1. A method for applying a temperature sensitive bioactive agent to the surface of a shaped polymeric substrate comprising:

(a) combining a matrix polymer having a melting point of about 100° C. or lower with a bioactive agent having a thermal decomposition point above said melting point, said matrix polymer being selected from the group consisting of ethylene acrylic acid copolymer, polycaprolactone, polyethylene adipate, polybutylene adipate, polyethylene azeleate and polyethylene methacrylic acid ionomer;

(b) melt compounding said matrix polymer and bioactive agent within the temperature range between said melting point and said decomposition point to give a homogeneous composition; and (c) extrusion coating said composition onto the surface of a shaped polymeric substrate at a temperature within said range.

2. The method of claim 1 wherein said polymeric substrate is a tubing.

3. The method of claim 1 wherein said polymeric substrate is composed of a polymer selected from the group of polymers consisting of polyacrylate, polystyrene, polyethylene, polypropylene, polytetrafluoroethylene, polyester, polyamide, polyvinyl and polyurethane.

4. The method of claim 1 wherein said bioactive agent is an anti-infective agent selected from the group consisting of methyl, propyl and butyl paraben, benzalkonium chloride, octenidine, alexidine, phenol, cresol, hexachlorophene, triphenyl bismuthine, nitrophenyl acetate, silver, cetyl pyridinium chloride, and bis biguanides.

5. The method of claim 1 wherein said bioactive agent is an antithrombogenic agent selected from the group consisting of heparin, prostaglandin, sulfated polysaccharide, urokinase, streptokinase and mixtures thereof.

6. The method of claim 1 wherein said combining step is performed by tumbling particles of said matrix polymer with particles of said agent.

7. The method of claim 1 wherein said melt compounding step is performed by extrusion compounding particles of said matrix polymer and particles of said bioactive agent at a temperature of 100° C. or less.

8. A method for applying an agent to the surface of a polymeric article comprising:
   a) preparing a homogeneous composition comprising a melt of a matrix polymer and a material selected from the group consisting of a bioactive agent and a quarternary ammonium salt, said matrix polymer being selected from the group consisting of ethylene acrylic acid copolymer, polycaprolactone, polyethylene adipate, polybutylene adipate, polyethylene azeleate and polyethylene methacrylic aid ionomer; and
   b) extrusion coating said composition onto a surface of a polymeric article at a temperature at which said material does not undergo any substantial thermal decomposition.

9. The method of claim 8 wherein said composition is a solution of said material in said melt.

10. The method of claim 8 wherein said composition is a suspension of said material in said melt.

11. The method of claim 8 further comprising reacting said salt subsequent to said extrusion coating step with an aqueous solution containing a bioactive agent which forms a complex with said bioactive agent.

12. A method for applying a temperature sensitive bioactive agent to the surface of a shaped polymeric substrate comprising:
   a) combining a matrix polymer having a melting point of about 100° C. or lower with a bioactive agent selected from the group consisting of heparin, chlorhexidine, a salt of chlorhexidine, benzalkonium chloride and methyl paraben, said matrix polymer being selected from the group consisting of ethylene acrylic acid copolymer, polycaprolactone, polyethylene adipate, polybutylene adipate, polyethylene azeleate and polyethylene methacrylic acid ionomer;
   b) melt compounding said matrix polymer and bioactive agent within the temperature range between said melting point and the decomposition point of said bioactive agent to give a homogeneous composition; and
   c) extrusion coating said composition onto the surface of a shaped polymeric substrate at a temperature within said range.

* * * * *